(12) United States Patent
Hur

(10) Patent No.: US 7,401,722 B2
(45) Date of Patent: Jul. 22, 2008

(54) CIRCULAR SURGICAL STAPLER WITH A DETACHABLE ANVIL

(75) Inventor: Yoon-Seok Hur, Seoul (KR)

(73) Assignee: Inha-Industry Partnership Institute, Incheon (KR)

( * ) Notice: Subject to any disclaimer, the term of this patent is extended or adjusted under 35 U.S.C. 154(b) by 0 days.

(21) Appl. No.: 10/553,002

(22) PCT Filed: Apr. 9, 2004

(86) PCT No.: PCT/KR2004/000828

§ 371 (c)(1),
(2), (4) Date: Oct. 11, 2005

(87) PCT Pub. No.: WO2004/089225

PCT Pub. Date: Oct. 21, 2004

(65) Prior Publication Data

US 2006/0201993 A1 Sep. 14, 2006

(30) Foreign Application Priority Data

Apr. 11, 2003 (KR) ...................... 10-2003-0022907

(51) Int. Cl.
*A61B 17/04* (2006.01)
*A61B 17/10* (2006.01)
(52) U.S. Cl. .................... 227/179.1; 227/19; 227/180.1; 227/181.1
(58) Field of Classification Search ............. 227/179.1, 227/19, 180.1, 181.1; 606/139, 219
See application file for complete search history.

(56) References Cited

U.S. PATENT DOCUMENTS

| 5,103,025 | A | | 4/1992 | Devant et al. ............... 549/387 |
|---|---|---|---|---|
| 5,205,459 | A | | 4/1993 | Brinkerhoff et al. ......... 227/179 |
| 5,271,543 | A | * | 12/1993 | Grant et al. .............. 227/179.1 |
| 5,333,773 | A | | 8/1994 | Main et al. ................... 227/179 |
| 5,350,104 | A | | 9/1994 | Main et al. ................... 227/179 |
| 5,533,661 | A | | 7/1996 | Main et al. ............... 227/176.1 |
| 5,669,918 | A | * | 9/1997 | Balazs et al. ................. 606/139 |
| 5,758,814 | A | * | 6/1998 | Gallagher et al. ......... 623/23.72 |
| 5,860,581 | A | | 1/1999 | Robertson et al. ......... 227/179.1 |
| 5,915,616 | A | * | 6/1999 | Viola et al. .............. 227/179.1 |
| 6,050,472 | A | | 4/2000 | Shibata ..................... 227/175.2 |
| 6,053,390 | A | | 4/2000 | Green et al. ............. 227/179.1 |
| 6,193,129 | B1 | | 2/2001 | Bittner et al. ............. 227/180.1 |
| 2005/0228446 | A1 | * | 10/2005 | Mooradian et al. .......... 606/215 |
| 2006/0135992 | A1 | * | 6/2006 | Bettuchi et al. ............. 606/219 |

\* cited by examiner

*Primary Examiner*—Brian D Nash
(74) *Attorney, Agent, or Firm*—Sheridan Ross P.C.

(57) ABSTRACT

The present invention relates to a circular stapler used for an operation of cutting off and suturing a jejunum, where a structure of the circular stapler is improved to facilitate manipulation thereof and to enhance the potential for success of the operation. The circular stapler comprises: a detachable anvil; a head section coupled to the detachable anvil and having a head section cover; and a cylindrical body which extends longs and of which the top end is coupled to the head section, and a recessed portion is formed in a side surface of the cylindrical body positioned under the head section cover. According to the circular stapler, it is possible to considerably reduce the potential for constricting the small intestine, to reduce the bleeding, which may be generated due to the stapling in a state where the tension is applied, and to reduce a risk that the small intestine is caught by the head section of the circular stapler during the suturing operation.

19 Claims, 12 Drawing Sheets

(A)

(B)

(C)

(A)

(B)

(C)

CIRCULAR SURGICAL STAPLER WITH A DETACHABLE ANVIL

BACKGROUND OF THE INVENTION (a) Field of the Invention

The present invention relates to an improved circular stapler, and more specifically, to a circular stapler used for an operation of cutting off and suturing a jejunum, where a structure of a head section is improved to facilitate manipulation thereof and to enhance the potential for success of the operation.

(b) Description of the Related Art

In operations of suturing both cut-off ends, such as esophagus reconstruction after extracting the esophagus, gastrectomy, and small or large intestinal resection, studies and developments of operative methods and instruments for more completely anastomosing or suturing both cut-off ends have been carried out continually.

Specifically, in operations on insides of human bodies, there are many difficulties when anastomosing an end of an esophagus and a jejunum at positions where it is difficult to carry out specific manipulations inside a diaphragm after the above suturing operations, that is, total gastrectomy, or when cutting off a rectum up to a portion close to an anus and then anastomosing the large intestine and the remaining rectum each other. That is, in order to anastomose the esophagus and the jejunum after the total gastrectomy, a major operation of cutting ribs and the diaphragm to enter a chest should have been performed. In a case of operation on the rectum, the anus should have been removed and the large intestine should have been exposed to the abdomen, so that a disorder of receiving excrements should be left.

One of the operative instruments developed to overcome the operative difficulties is an intraluminal stapler, which is used for esophagus to jejunum anastomosis or intestine to intestine anastomosis, or cutting off a specific portion and anastomosing blood vessels each other. The intraluminal staplers are divided into circular staplers and linear staplers. The circular staplers are used mainly for anastomosing esophagus to jejunum in the total gastrectomy or anastomosing the jejuna each other and the linear staplers are used mainly for closing ends of cut intestines. Circular staplers having a diameter of 25 mm, 28 mm, 29 mm, 31 mm, 33 mm, etc. are put on the market.

Such a circular stapler is a product recognized officially by U.S. FDA (Food and Drug Administration), which is used as follows. An anvil is inserted into an upper end of the intestine to be anastomosed, the end of the intestine is tied, a cylindrical body having a head section including staples fixed in a circular shape and a cylindrical blade is inserted into a lower end of the intestine, a side surface of the intestine is pierced by a trocar tip, the trocar tip is coupled and fixed firmly to the anvil, the anvil and the head section come in close contact with each other and are stapled by turning an adjusting screw, and the intestines interposed therebetween are cut off, thereby anastomosing the ends of both intestines. A structure of the conventional circular stapler will be described in more detail with reference to U.S. Pat. No. 5,104,025.

U.S. Pat. No. 5,104,025, registered on Apr 14, 1992, discloses a conventional circular stapler having a detachable anvil. The circular stapler disclosed in FIG. 1 of the U.S. Pat. No. 5,104,025 is the same as the circular stapler 100 of FIG. 5. In FIG. 5, reference numerals, which are different from those of the circular stapler disclosed, in the U.S. Pat. No. 5,104,025, are used to explain the circular stapler 100 of a prior art for convenience. As shown in FIG. 5, the circular stapler 100 roughly comprises an anvil 10 and a cylindrical body 40, and the anvil 10 has a staple support 11 and an anvil shaft 21 and is detachably coupled to the cylindrical body 40. A trocar tip 22 passes through the cylindrical body 40, and a lower portion of the cylindrical body 40 is provided with a handle 50, a trigger 60, a safety 70 and an adjusting screw 80.

Although a method for using the circular stapler disclosed in U.S. Pat. No. 5,104,025 is not illustrated therein, such a circular stapler can be explained to be used hereinafter with reference to FIGS. 5 to 8.

A method of actually operating on the inside of a human body using the circular stapler is shown in FIGS. 6A to 6C. First, as shown in FIG. 6A, for example, A Rouxen Y method is used for anastomosing the esophagus to the jejunum after the total gastrectomy. At that time, a method of anastomosing an end of the esophagus to a side of the jejunum is used mainly for this operation. That is, the anvil 90 of the circular stapler is inserted into an end of the esophagus E to protrude the anvil shaft 92 outwardly, and then the lower portion is fixed temporarily with a thread. Next, the head section 94 of the circular stapler is inserted into an end of the jejunum J to be connected and the jejunum is bent, and then the trocar 93 is allowed to pierce the jejunum and to approach the anvil shaft 92.

Next, as shown in FIG. 6B, the anvil 90 and the head section 94 are connected by coupling the trocar tip to the anvil shaft 92, and the anvil 90 and the head section 94 become closer to each other by turning the adjusting screw provided at an end of the circular stapler, thereby allowing both to engage with each other. When the anvil 90 and the head section 94 come in close contact with each other, the safety of the circular stapler is released, the handle is grasped, and then the trigger is pressed. When the trigger is pressed, the cylindrical blade and the staples are projected from the head section 94, whereby the intestines between the anvil 90 and the head section 94 of the circular stapler are cut off and the end of the esophagus and the side of the jejunum are connected through the staples.

A state where the jejunum and the esophagus are anastomosed in this way is shown in FIG. 6C. After anastomosing the end of the esophagus E to the side of the jejunum J, the circular stapler is pulled out, and the opened portion of the jejunum J is sutured by stapling the opened portion with the linear stapler 910. As a result of this operation, the end of the esophagus is connected to the side surface of the jejunum to form a shape in which one tube is divided into two tubes, whereby only the portion through which food proceeding along the esophagus pass to proceed toward the lower portion of the jejunum is left opened.

Conventionally, since the portions to be connected of a human body could be easily connected using the above circular stapler to innovatively improve the operative methods, the complex operative processes are simplified very much and leakage from the anastomosed portion or the number of bleeding times are reduced, thereby considerably lowering the complication after operation and the mortality rate during operation. However, the conventional circular stapler causes several severe problems in the esophagus to jejunum anastomosis due to its structural features. These problems will be described in more detail with reference to FIG. 7.

(A) through (C) of FIG. 7 conceptually illustrate variation in diameter of the jejunum before and after performing the esophagus E to jejunum J anastomosis using the conventional circular stapler. Here, (A) of FIG. 7 schematically shows the shape of the jejunum before the operation, where point A is a portion which should be pierced by the circular stapler and which should be connected to the center of the esophagus. As shown in (A) of FIG. 7, the jejunum before the operation has almost the same inner diameter, where L1≈L2≈L3.

In this way, by inserting the head section 94 into the end of the jejunum J, piercing the side surface of the jejunum J with the trocar tip 93, and thus connecting the jejunum to the esophagus E, the state shown in (B) of FIG. 7 is obtained. That is, when the circular stapler having a cylinder-shaped head section 94 is inserted into the jejunum J, the circular stapler is tightly fitted to the inside of the jejunum J, and in this state, in order to connect the jejunum to the end of the esophagus E, the jejunum J should be bent at about 180° and a portion to be stapled by the circular stapler should be exposed. At that time, one end of the jejunum into which the circular stapler is inserted holds a circular sectional shape, while the other end of the jejunum through which food should actually pass is drawn due to application of tension. The end of the esophagus E is anastomosed to the jejunum by carrying out the stapling.

As shown in (B) of FIG. 7, when the head section 94 of the circular stapler is connected to the esophagus E, force is applied toward the top end of the head section 94 of the circular stapler and thus the tension on the jejunum is applied upwardly, so that a portion AB is stretched more than a portion A'B' due to the tension. If the esophagus E is connected to the jejunum J in a state where the portion AB is abnormally stretched more than the portion A'B' as described above, the state shown in (C) of FIG. 7 is obtained, so that the diameter L1 (length of AA") of the jejunum to be restored to the original state is too small and may be rather closed. That is, since L1 is still shorter than L2 (length of BB') and L3 (length of CC'), food passing through the esophagus does not proceed to the left jejunum for digestion, proceeds to the right jejunum, and is stored in the closed portion, it is easy to cause indigestion and the potential for sequela is large even after the operation.

Furthermore, in the anastomosed portion of the esophagus, the tension is applied uniformly on its circular section and the staples are uniformly distributed, but since the tension on the anastomosed portion in the side surfaces of the jejunum is not uniform and the anastomosed portion of the jejunum is stapled in a state where the AC side is more stretched than the AB side, relatively more jejunum tissues are stapled at the AB side. A proper tension is applied to point B. Therefore, the bleeding is much generated at an intermediate position between A and B. The non-uniform tension may constrict the anastomosed portion.

Specifically, the above problem may become severer because in most surgical operations, the operation wounds are invisible and senses of hands is absolutely relied on, and still severer because most surgeons do not consider the above problems as problems particular to the conventional circular staplers, but as their own technical mistakes.

On the other hand, (A) and (B) of FIG. 8 are conceptual diagrams illustrating another problem that may be caused in the operation using the conventional circular stapler. In actual operations, since the surgeons cannot see the shape of anastomosed wounds and handle the circular staplers only relying upon the sense of hands, the jejunum side through which food passes may be too folded and much relaxed, and may have a very large surface area compared with the circumference of the jejunum. As a result, the internal mucosa of the jejunum forming the folds may be interposed between the anvil 90 and the head section 94 and thus may be cut off.

That is, since the jejunum is severely constricted due to the technical mistakes as shown in (A) of FIG. 8 and portions not associated with the anastomosis are interposed between the anvil 90 and the head section 94 of the circular stapler and are cut off to form the shape shown in (B) of FIG. 8, the left side of the jejunum may be closed and thus a re-operation may be necessary.

This state may cause very severe complications. Since the inner diameter of the jejunum side through which food passes is very small, patients have difficulties in swallowing food. Further, since the tension of the anastomosed wound at the side of the jejunum is not uniform, the bleeding may be caused in the anastomosed wound and may be constricted.

SUMMARY OF THE INVENTION

The present invention is contrived to solve the problems of the conventional circular staplers described above, such as the bleeding or the constriction of the jejunum after operation, by changing the shape and structure of a head section of a circular stapler.

Also, the present invention is contrived to solve the problems such as difficulties in use of a circular stapler, failure of operation, etc., and the present invention provides a circular stapler having a special structure which does not allow inner jejunum portions to be folded.

A circular stapler comprises: a detachable anvil; a head section coupled to the detachable anvil and having a head section cover; and a cylindrical body that longitudinally extends and one end thereof is coupled to the head section, wherein a recessed portion is formed in a side surface of the cylindrical body positioned under the head section cover.

Here, the head section cover may have a circular plate shape.

Further, the head section may comprises: a cylindrical blade; a staple holder having a plurality of staple slots which surround the outer circumferential portion of the cylindrical blade, staples being provided inside the staple slots; a push member provided with a protruded portion inserted into the staple slots for pushing the staples; and a support positioned under the push member and having a circular plate-shaped top for pushing the push member.

The push member may have a circular plate-shaped housing and the protruded portion may be formed on the circular plate-shaped housing.

The push member may be coupled integrally to the support.

The circular plate-shaped top may be made of steel.

The length of the head section cover in a longitudinal direction of the cylindrical body may be set to 15 through 18 mm.

The cylindrical body may have an arch shape.

The circular stapler may further comprise a detachable cap coupled and fixed to the recessed portion.

The circular stapler may further comprise a shaft which passes through the head section and the cylindrical body and extends long, and it is preferable that the diameter of the shaft is set to 1.0 through 1.5 mm.

The circular stapler may further comprise a trigger which is provided at a lower portion of the cylindrical body to oppose the recessed portion and which pushes the support.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE PREFERRED EMBODIMENTS

The present invention will now be described in more detail with reference to the accompanying drawings and most preferable embodiments of the present invention which can be put into practice by those skilled in the art. The embodiments only exemplify the present invention and thus the present invention should not be construed as being limited to the embodiments.

Figure 1:
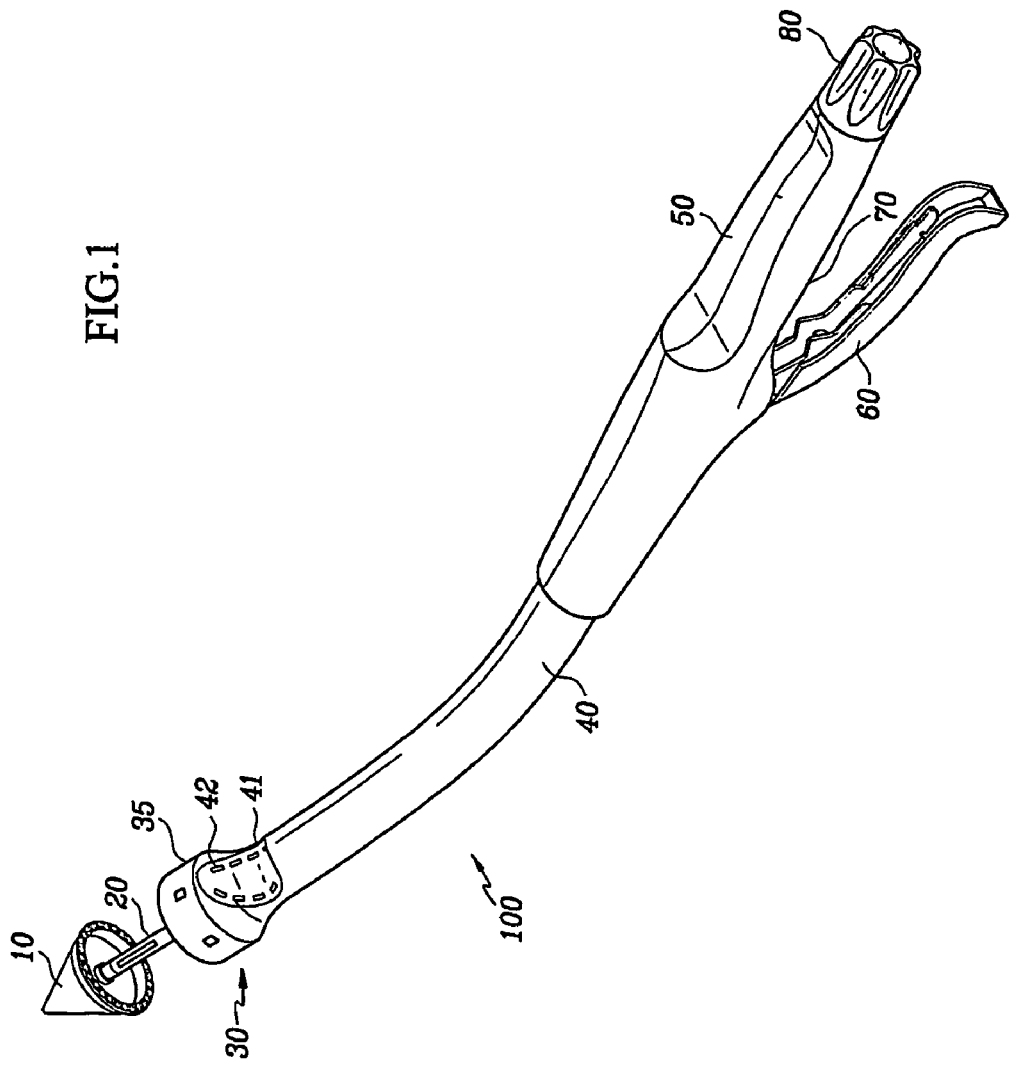
FIG. 1 is a perspective view schematically illustrating a circular stapler according to the present invention.

Hereinafter, the present invention will be described in detail with reference to FIGS. 1 to 4B. FIG. 1 is a schematic perspective view of a circular stapler according to the present invention, and shows the whole shape of the circular stapler according to the present invention. As shown in FIG. 1, the circular stapler 100 according to the present invention comprises an anvil 10, a head section 30, a cylindrical body 40, a handle 50, a trigger 60, a safety 70, and an adjusting screw 80, and the anvil 10 is detachable. The head section 30 has a head section cover 35, and is coupled to a top end of the cylindrical body 40. An anvil shaft of the anvil 10 is coupled to a trocar tip of the cylindrical body 40 each other, thereby forming a shaft 20. The shaft 20 extends long through the head section 30 and the cylindrical body 40.

The head section cover 35 has a circular plate shape. That is, in a conventional circular stapler, a head section cover has been formed to have a length of about 25 to 30 mm in a longitudinal direction of a cylindrical body, but in the circular stapler 100 according to the present invention, the length of the head section cover 35 in the longitudinal direction of the cylindrical body 40 is largely reduced into a length of 15 to 18 mm, thereby forming a circular plate shape. Accordingly, the length of the head section 30 including the head section cover 35 is largely reduced. Further, as shown in FIG. 1, a recessed portion 41 is formed at the top side of the cylindrical body 40 under the header section cover 35, thereby securing an empty space. Grooves 42 are formed inside the recessed portion 41. The shapes of the recessed portion 41 and the grooves 42 are given only as an example, and thus the present invention is not limited to the above shapes.

Figure 2A:
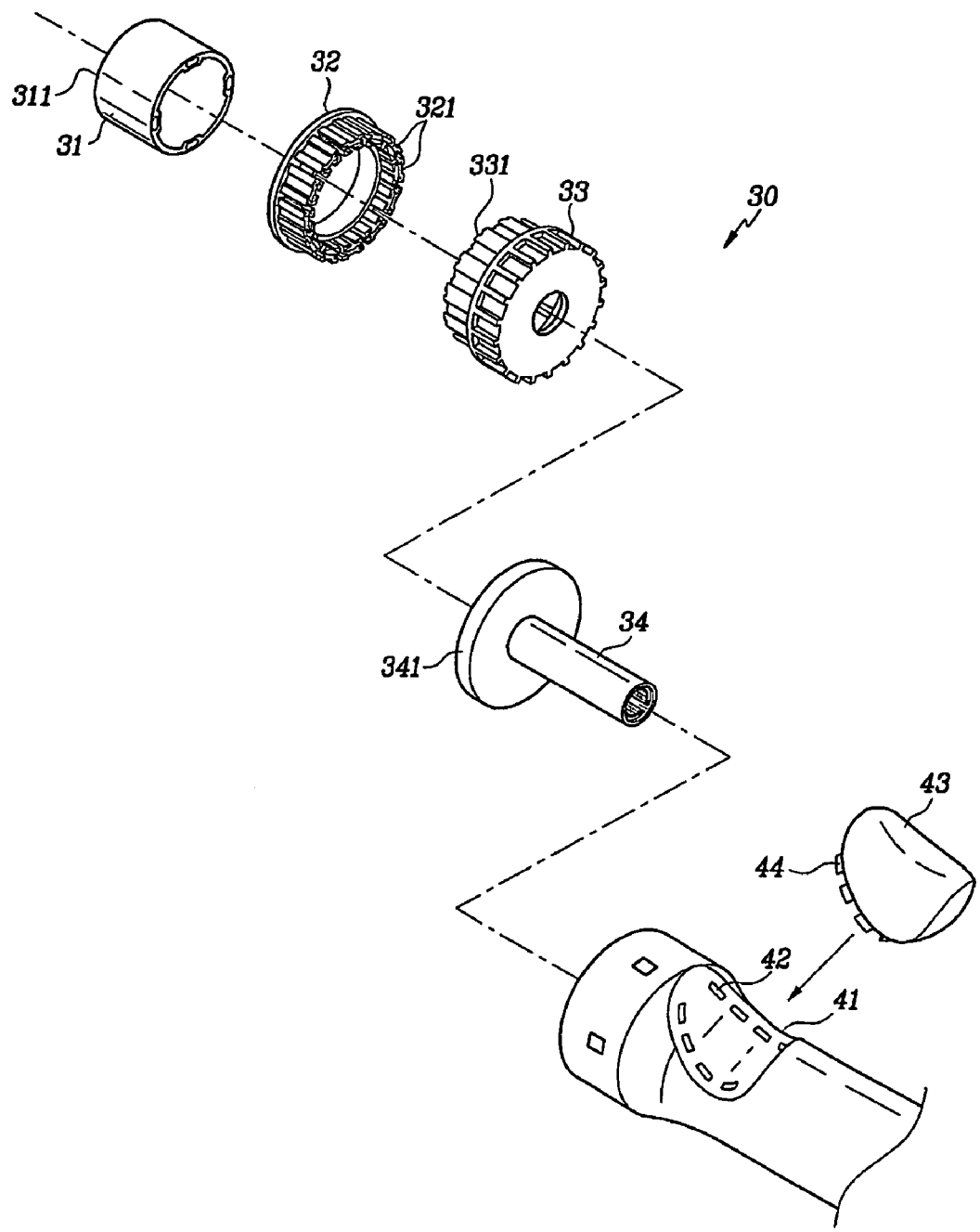
FIGS. 2A to 2C are exploded perspective views illustrating various head sections of the circular stapler according to the present invention.
Figure 2B:
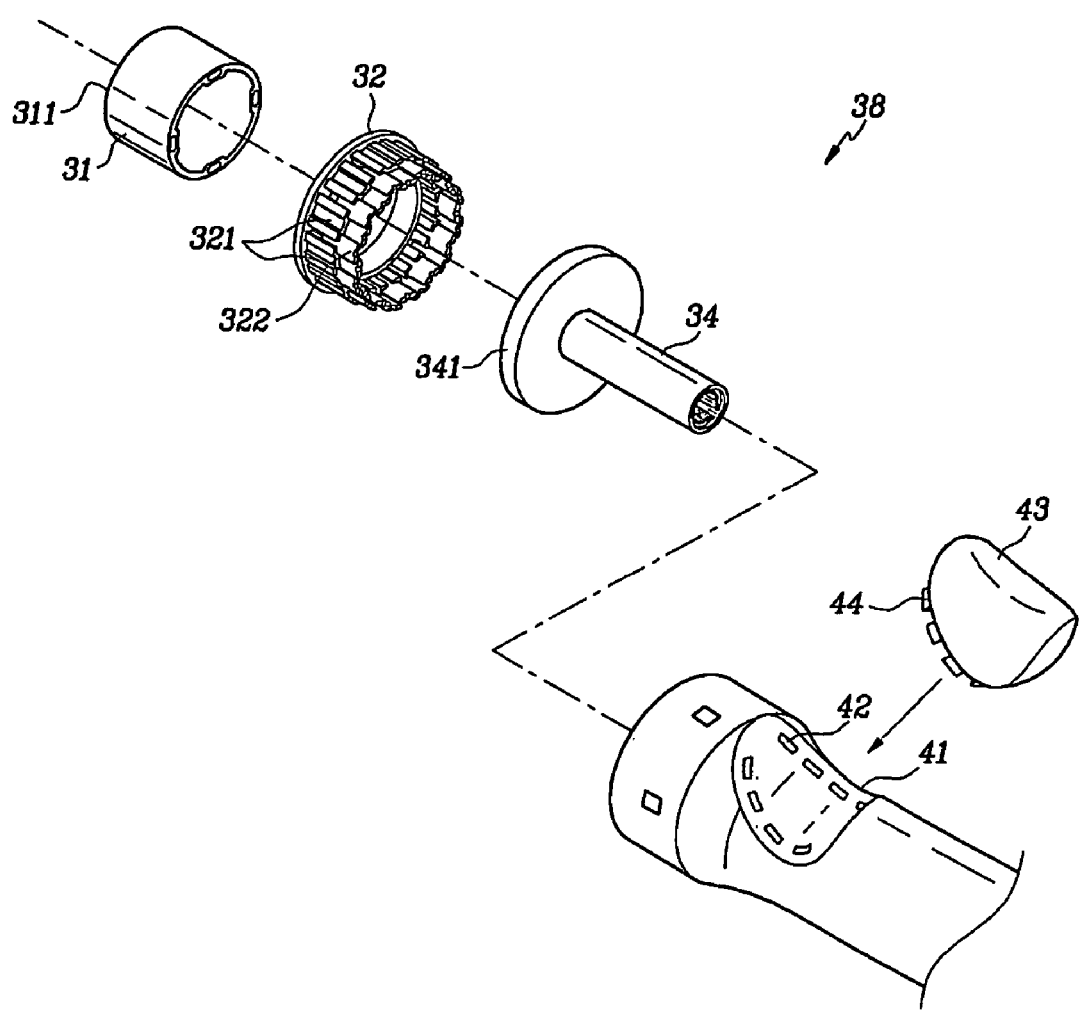
Figure 2C:
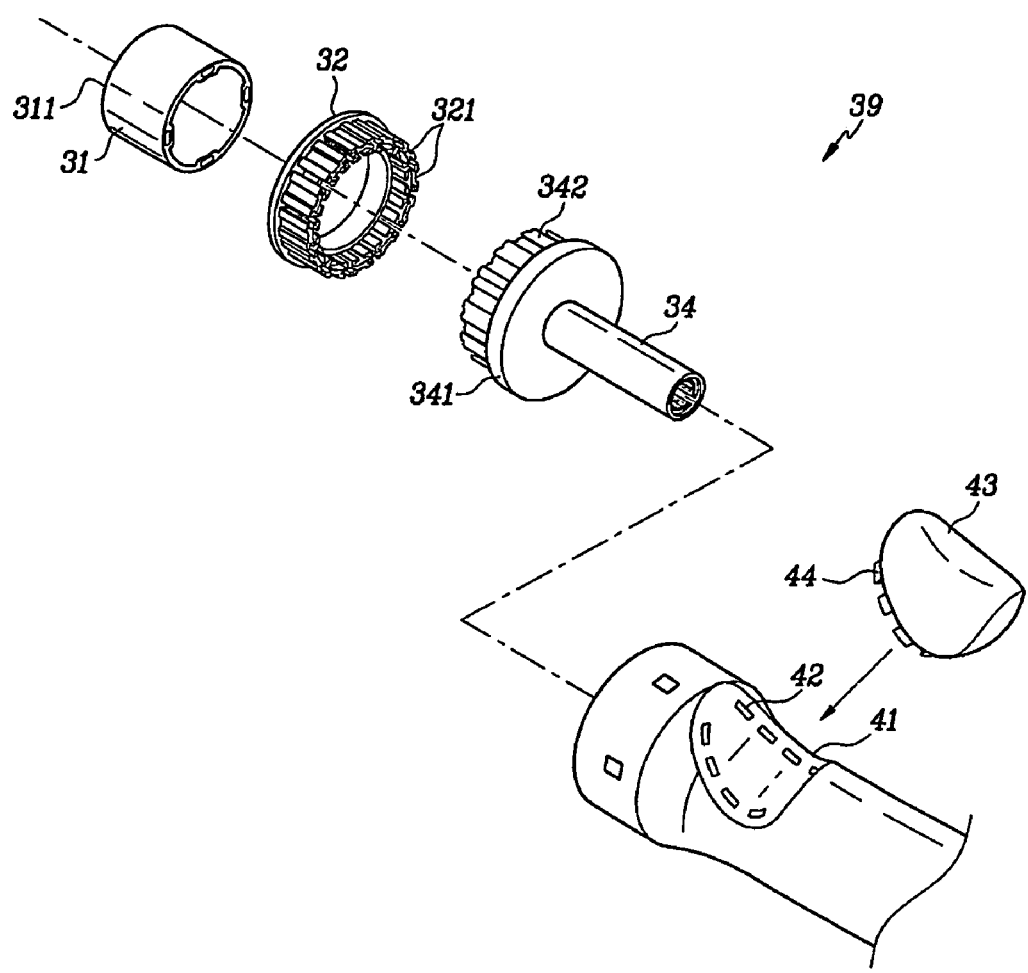

The cylindrical body 40 is curved in an arch shape to facilitate the insertion of the head section 35 during operation, and the trigger 60 is provided at a lower portion of the cylindrical body 40 to oppose the recessed portion 41 and pushes a support 34 (see FIGS. 2A to 2C). In consideration of a position into which the head section 35 is inserted, by positioning the trigger 60 to oppose the head section 35, it is easy to grasp the trigger 35 with a hand to facilitate the manipulation thereof when the head section 35 is inserted into the operation wound.

The shaft 20 has a diameter of 1.0 to 1.5 mm. By setting the diameters of the shaft 20 and the support 34 (see FIGS. 2A to 2C) surrounding the shaft to be as small as possible, the recessed portion 41 under the head section 30 can be formed easily regardless of the diameters of the shaft 20 and the support 34.

In the circular stapler 100 according to the present invention, the thickness of the head section cover 35 is designed in accordance with the circumferential length of a small intestine of a general person, because the head section of the circular stapler is brought into close contact with a side surface of the intestine when inserting the head section is inserted into the intestine.

That is, since the inner diameter of a small intestine of a general person is about 27 to 33 mm, the inner circumferential length (inner diameter × π) of the small intestine can be calculated as about 84.8 to 103.6 mm. Since the top of the head section comes in contact with a side surface of the small intestine when inserting the head section of the circular stapler according to the present invention, it can be considered that the length obtained by subtracting double the diameter (inner diameter of the small intestine: 27 to 33 mm) of the head section cover from the inner circumferential length (84.8 to 103.6 mm) is double the length of the head section cover. Therefore, since the length of the head section cover amounts to about 15.39 to 18.81 mm in maximum, the length of the head section cover can be calculated as 18.81 mm or less theoretically. However, since some length is required for providing components in the head section, it is preferable that the length of the head section cover in the circular stapler according to the present invention is set to 15 through 18 mm.

Now, inner structures of the circular staplers according to first to third embodiments of the present invention will be described in more detail with reference to FIGS. 2A to 2C, respectively. These embodiments according to the present invention are given only to exemplify the present invention, and thus the present invention is not limited to the embodiments.

First Embodiment

FIG. 2A is an exploded view schematically illustrating an inner structure of the head section 30 of the circular stapler according to the first embodiment of the present invention. As shown in FIG. 2A, the head section of the circular stapler according to the present invention comprises a cylindrical blade 31, a staple holder 32, a circular plate-shaped housing 33, a support 34, and a head section cover 35. Pierced holes are formed at the centers of all components of the head section 30 of the circular stapler, thereby providing a space in which the shaft coupled to the anvil can be moved up and down. As shown in FIG. 2A, the housing 33 sequentially accommodates the cylindrical blade 31 and the staple holder 32. Specifically, staple slots 321 for accommodating a plurality of staples are formed in the staple holder 32, and a plurality of protruded portions 331 being inserted into the staple slots 321 to push the staples are formed in the circular plate-shaped housing 33 along the circumference thereof.

In this structure, when the trigger provided at the lower portion of the circular stapler is pressed, the support 34 extending in the longitudinal direction of the circular stapler goes up to push up the circular plate-shaped housing 33, the protruded portions 331 formed on the circular plate-shaped housing 33 pushes up the staples accommodated in the staple slots 321 of the staple holder 32, the portions interposed between the anvil and the head section are cut off with a blade portion 311 of the cylindrical blade 31 at the same time as the suturing of both sides of the intestines with the staples.

Specifically, a top 341 of the support 34 is formed out of a steel plate, so that the stapling can be easily performed through application of strong force thereto when pushing the circular plate-shaped housing 33. The staples are made of titanium which is a living body-friendly material. Titanium is a material providing a strong intensity and is used for golf clubs, but in the present invention, the support 34, of which the top is made of steel, is enough to simply bend the staples made of titanium and perform the stapling. The lower portion of the support 34 may be made of plastic material. Although the lower portion of the support 34 is shown to be short in FIG. 2A, this is given only to exemplify the present invention, and a structure that the lower portion is lengthened to allow the trigger to directly apply force to the lower portion may be also employed. In consideration of the recessed portion 41 formed at one side under the head section cover 35, it is preferable that the support 34 is formed to have such a small diameter that the shaft can pass, and a structure that the lower portion of the support 34 is exposed from the recessed portion and is movable may be employed.

As shown in FIG. 2A, in the circular stapler according to the present invention, the recessed portion 41 is formed in an upper side surface of the cylindrical body positioned under the head section cover 35. The recessed portion 41 provides an empty space during the operation for end to side anastomosis, whereby the constriction of the intestines can be prevented and the bleeding can be prevented.

Further, since grooves 42 are formed in the recessed portion 41, the cap 43 is coupled to the recessed portion through the protruded portions 44 formed in the cap 43 to form an original smooth shape. Therefore, the circular stapler according to the present invention can be also utilized for the operation for end to end anastomosis which may have difficulties due to the recessed portion, in addition to the operation for end to side anastomosis.

In the circular stapler according to the first embodiment of the present invention, if the length of the head section cover 35 is set to 15 through 18 mm, the components constituting the head section 30 can be formed such that the staple holder 32 has a length of about 8 to 10 mm, the housing 33 of which apart of the tip is inserted into the staple holder 32 has a length of about 12 to 15 mm, and the top 341 of the support 34 has a length of about 2 to 4 mm. The length of the respective components constituting the head section 30 are given only to exemplify the present invention, and thus the present invention is not limited to these lengths.

Second Embodiment

FIG. 2B is an exploded view schematically illustrating the inner structure of the head section of the circular stapler according to the second embodiment of the present invention. Hereinafter, the same elements as the first embodiment will not be described, and only elements different from the first embodiment will be described.

As shown in FIG. 2B, in the second embodiment of the present invention, the push member 322 for pushing the staples are fixed to the staple slots 321 and pushes up the staples with upward movement of the support 34. The push member 322 may be made of metal or plastic, and since the push member is fixedly inserted into passages formed in the staple slots 321, the push member is never separated. When the trigger is pressed, the top 341 of the support 34 comes in contact with the lower end of the push member 322 and pushes up the push member 322, whereby the upper end of the push member 322 pushes up the staples.

Specifically, in the second embodiment of the present invention, since the thickness of the head section can be formed smaller by omitting the circular plate-shaped housing of the first embodiment, it is possible to more elastically adjust the thicknesses of the other components of the head section.

Third Embodiment

FIG. 2C is an exploded view schematically illustrating the inner structure of the head section of the circular stapler according to the second embodiment of the present invention. Hereinafter, the same elements as the first embodiment will not be described, and only elements different from the first embodiment will be described.

As shown in FIG. 2C, in the third embodiment of the present invention, the push member 342 is coupled integrally to the support 34, and pushes up the staples with upward movement of the support 34. It is preferable that the push member 342 is made of steel, because the push member is coupled integrally to the top of the support 34. The push member 34 is fixed to the staple slots 321 and is moved up and down.

The handle and the trigger of the circular stapler according to the embodiments of the present invention are familiar to those of ordinary skill in the art, and thus description thereof will be omitted.

An operational example of the circular stapler according to the present invention will be described in detail with reference to FIG. 3. (A) of FIG. 3 is a diagram schematically illustrating the shape of a small intestine (jejunum) before the operation, (B) of FIG. 3 is a diagram schematically illustrating the inner shape of the jejunum when the esophagus is connected to the jejunum by using the circular stapler according to the present invention, and (C) of FIG. 3 is a diagram schematically illustrating the shape in which the esophagus is connected to the jejunum after completion of the operation using the circular stapler according to the present invention.

Figure 3:
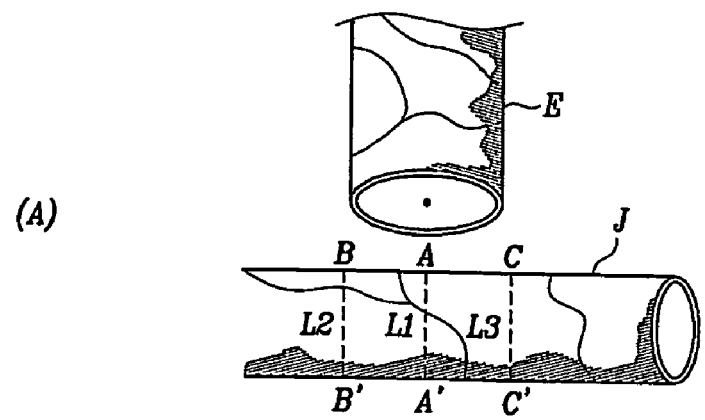
FIG. 3 is a conceptual diagram illustrating in a case where an operation is performed using the circular stapler according to the present invention.
Figure 3:
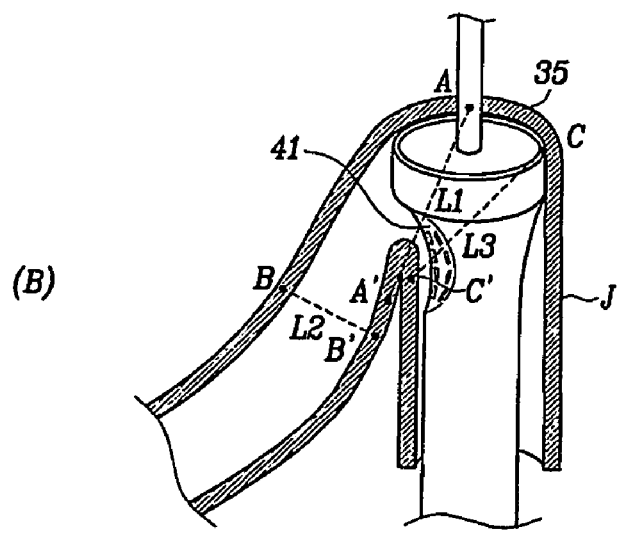
Figure 3:
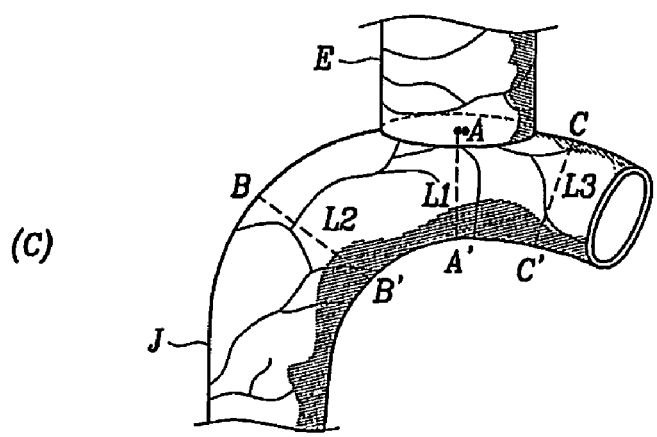

As shown in (A) of FIG. 3, the inner diameters L1 (length of BB'), L2 (length of AA'), and L3 (length of CC') of the jejunum before the operation are almost equal each other. The jejunum J is connected to the esophagus with the circular stapler according to the present invention, after piercing the side surface of the jejunum and bending the jejunum by 180° as shown in (B) of FIG. 3. In the circular stapler according to the present invention, the head section cover 35 has a small thickness and a circular plate shape and the recessed portion 41 is formed in the upper portion of the cylindrical body under the head section cover 35 to form an empty space. Therefore, when the jejunum J is lifted by inserting the circular stapler according to the present invention into an end of the jejunum J, a small tension is applied to the jejunum J and the probability that the folded portions of the jejunum J as shown in the left side of (B) of FIG. 3 comes in contact with the circular stapler become lower, so that there is no risk that the jejunum J not relating to the anastomosis is drawn up. Therefore, there is no risk that the jejunum J is stretched non-uniformly due to the tension applied to only a part of the jejunum J and that the jejunum J is constricted. That is, as shown in (C) of FIG. 3, since the inner diameters L1, L2, and L3 of the jejunum are almost equal each other even after the operation, food passing through the esophagus can easily proceed toward the left jejunum.

On the other hand, it may be considered that the force applied for coupling the anvil and the head section cannot be uniform due to the specific structure according to the present invention to cause a defect in the coupling. However, in the present invention, the coupling is not carried out with only the force from the lower portion of the head section, but the force is applied from the lower portion of the head section in a state where the anvil and the head section come in close contact with each other to carry out the coupling, thereby causing no problem.

It is preferable that the length of the head section cover in the longitudinal direction of the cylindrical body is about 15 to 18 mm. As a result, since the head section cover of the circular stapler does not cover the whole inner diameter of the jejunum J and thus the margin exists in the space, it is possible to reduce the potential for constriction of the jejunum. In addition, since the length of the head section cover becomes smaller and thus the weight of the head section is reduced, the tension applied to the anastomosed surface of the jejunum is also reduced, so that the anastomosis is not carried out in a state where the jejunum is stretched. Accordingly, it is not necessary to sparsely fasten the staples due to the non-uniform tension and it is possible to prevent the bleeding due to the difference in tension. By forming the head section cover of the circular stapler with the length described above and forming the recessed portion under the head section cover, it is possible to simply solve the problems of the conventional circular stapler.

The present invention will be explained below with reference to an experimental example of the present invention. The experimental example of the present invention is merely to illustrate the present invention and the present invention is not limited thereto.

Experimental Example

Figure 4A:
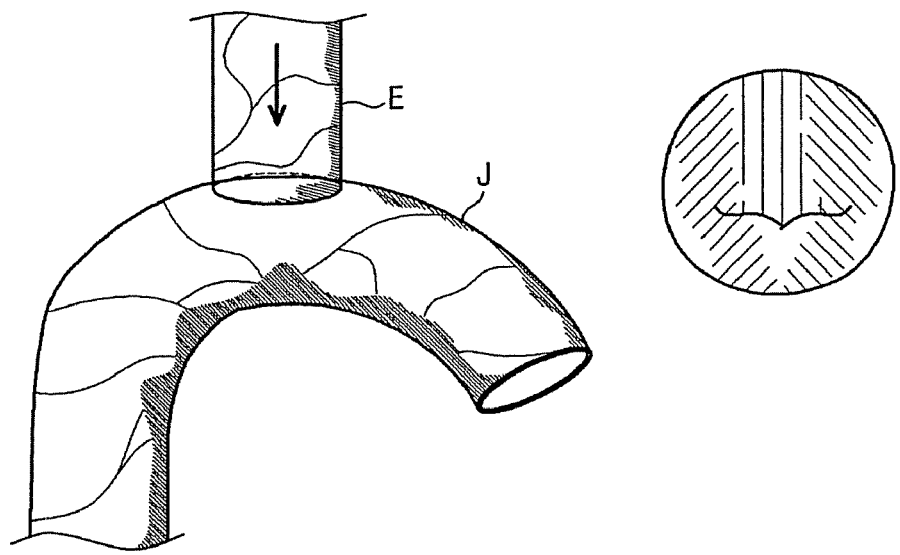
FIGS. 4A and 4B are diagrams illustrating operation wounds when using the circular staplers of an experimental example of the present invention and of a comparative example of a prior art conventional circular stapler, respectively.

An operation is processed by using a circular stapler as illustrated in FIG. 1. FIG. 4A is a diagram illustrating the operation wound when using the circular stapler illustrated in FIG. 1 of the experimental example.

As shown FIG. 4A, when using the circular stapler of the experimental example, the left and right inner diameters of the jejunum J after the operation are almost equal each other. When the operation is performed using the circular stapler of the experimental example, as shown in an enlarged circle of FIG. 4A illustrating the inner section of the operation wound as seen from the esophagus E, no bent portion exist in the jejunum J and no tension is not applied to the mucosa, so that no ridge is generated and only normal mucosa is shown. Therefore, since the inner diameter of the jejunum J is kept equal to that before the operation, food passing from the esophagus can proceed without problem.

Comparative Example

Figure 4B:
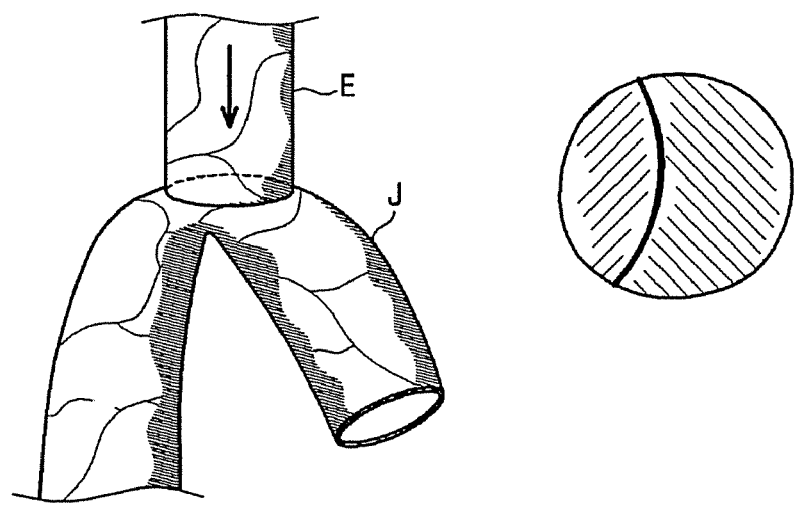
Figure 5:
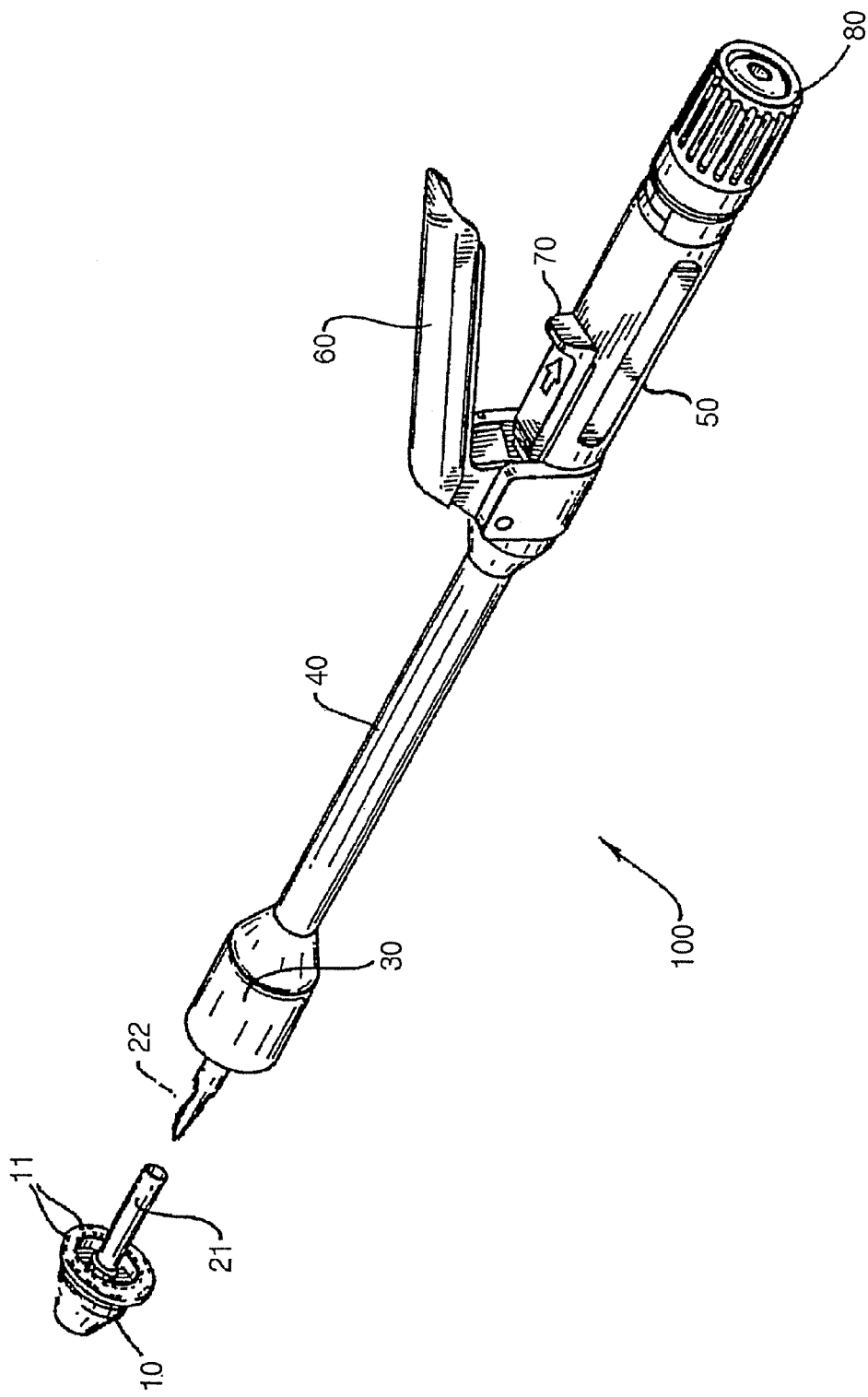
FIG. 5 is a perspective view schematically illustrating the prior art conventional circular stapler.
Figure 6A:
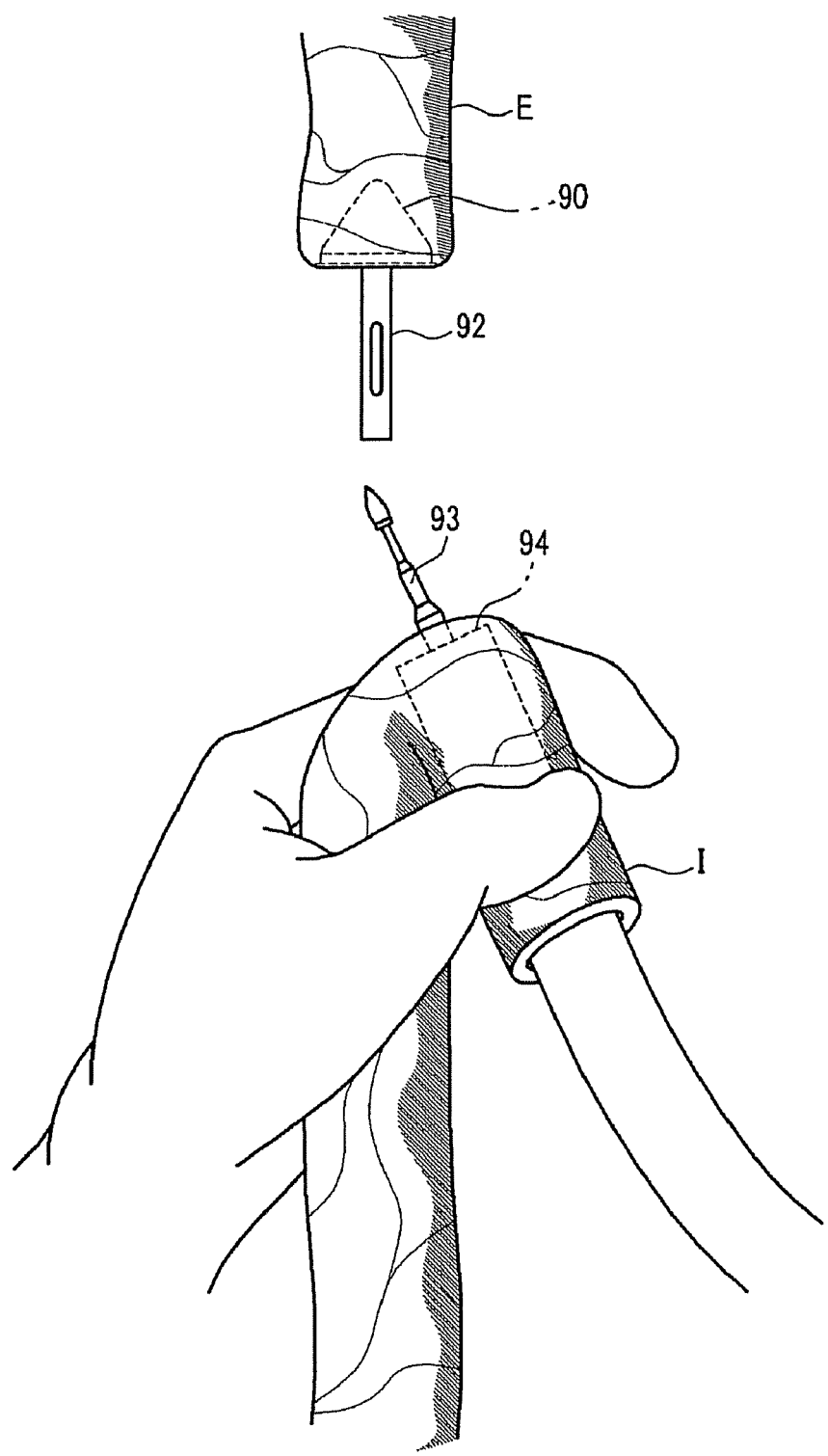
FIGS. 6A to 6C are diagrams illustrating respective steps of an operation using the prior art conventional circular stapler.
Figure 6B:
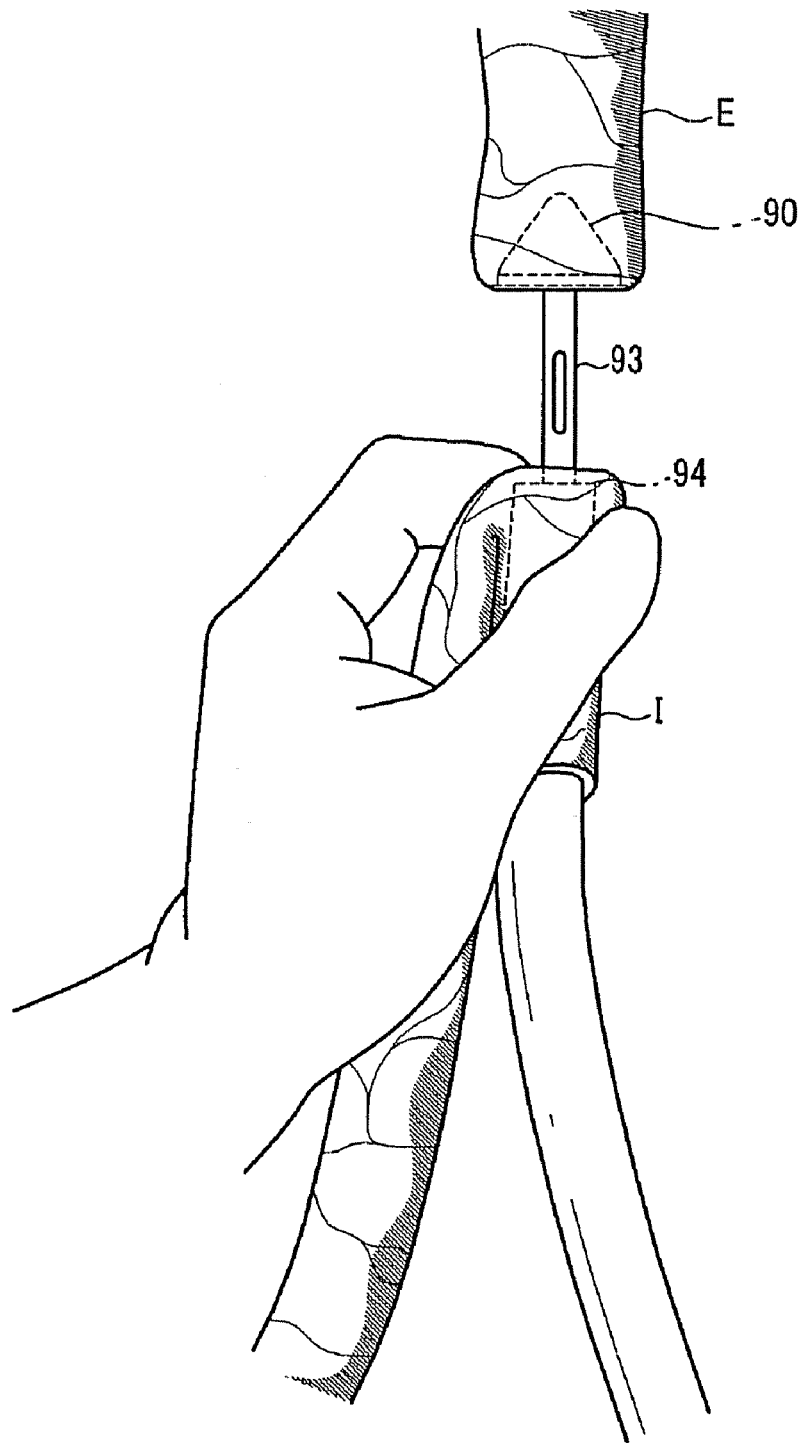
Figure 6C:
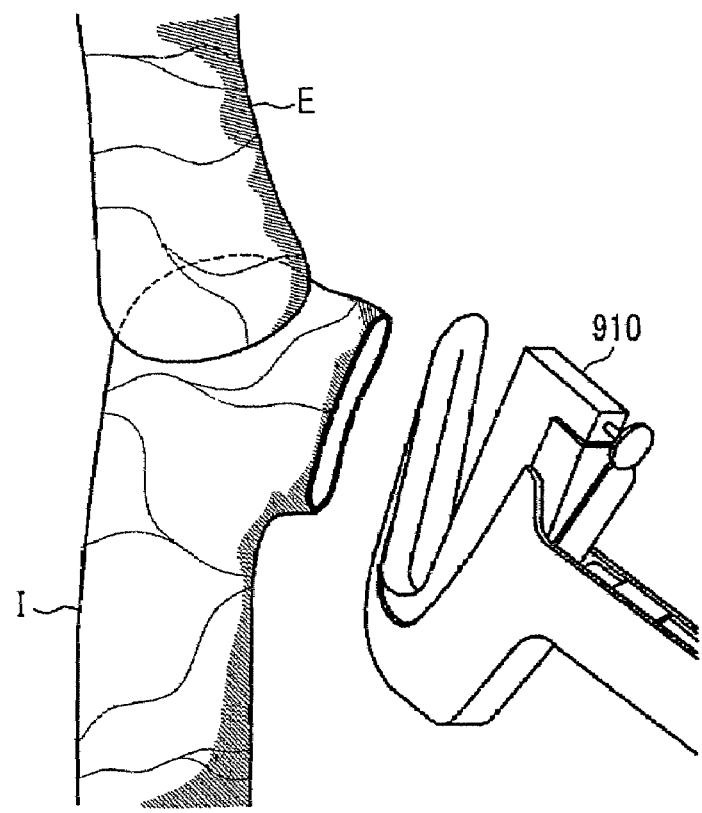
Figure 7:
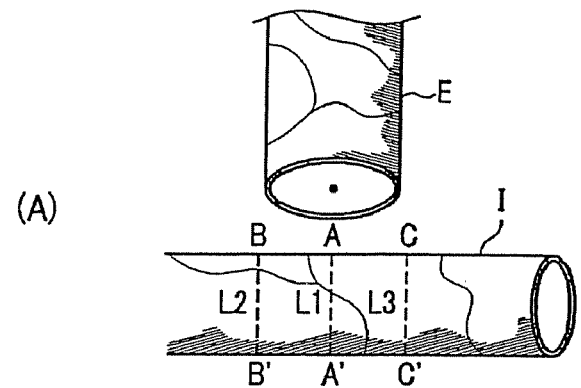
FIG. 7 is a conceptual diagram illustrating a problem of the operation using the prior art conventional circular stapler.
Figure 7:
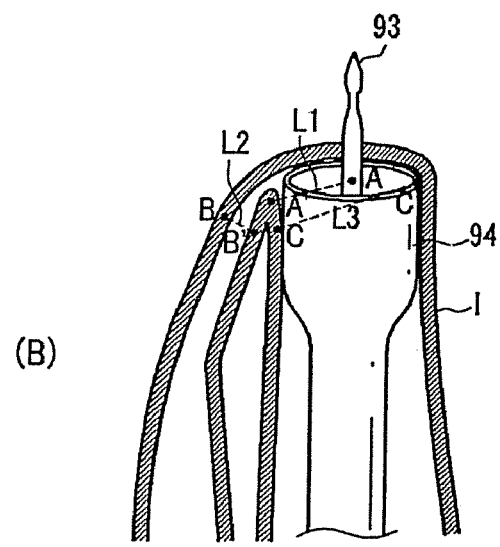
Figure 7:
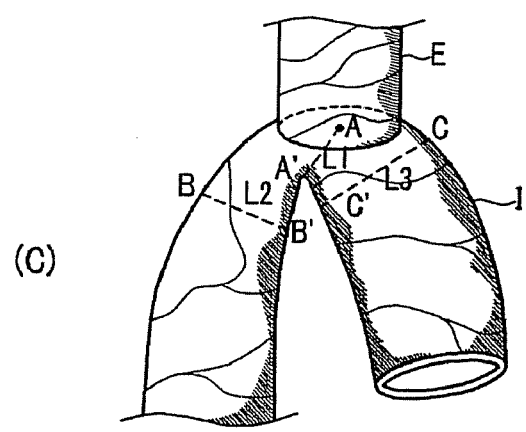
Figure 8:
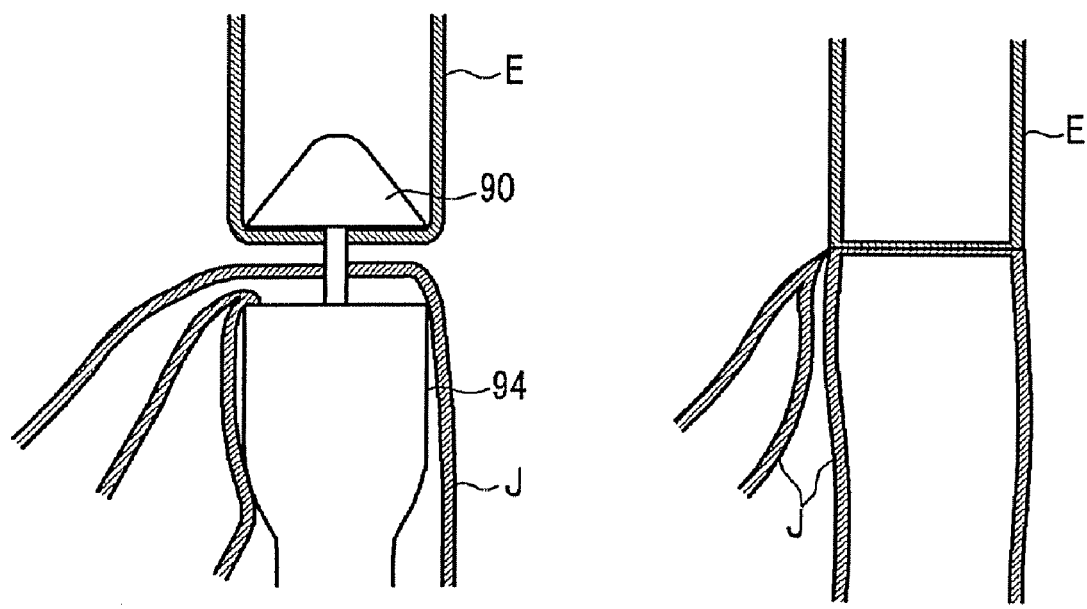
FIG. 8 is a conceptual diagram illustrating another problem of the operation using the prior art conventional circular stapler.

An operation is processed by using a circular stapler of a prior art as illustrated in FIG. 5. FIG. 4B is a diagram illustrating the operation wound when using the circular stapler illustrated in FIG. 5 of the comparative example. When the circular stapler of the comparative example, as shown FIG. 4B, the anastomosis is performed with non-uniform tension and thus the width of the jejunum J is reduced, thereby causing problems after the operation. That is, the staples are fastened in the end portion of the esophagus E with uniform tension, but are not uniformly fastened in the jejunum J.

Referring to an enlarged circle of FIG. 4B illustrating the inner section of the operation wound as seen from the esophagus E, it can be seen that the jejunum J is bent to form the left portion of the jejunum J and the right portion of the jejunum J and the mucosa is drawn to form the ridges. Specifically, the left portion has such a small width difficult to pass food, and the right portion which should be sutured after the operation has a rather large width. As can be seen from the sectional view, since food from the esophagus E does not proceed through the left portion of the jejunum J but stays in the right portion of the jejunum J, severe problems may be caused in digestion, etc.

As described above, although a case where the esophagus and the jejunum are anastomosed using the circular stapler according to the present invention has been described in detail, the connection intestines are given only to exemplify the present invention, and the present invention is not limited to the connection intestines. For example, the circular stapler according to the present invention may be used for anastomosing the small intestines each other.

As described above, in the circular stapler according to the present invention, since the recessed portion is formed under the head section cover to secure an empty space, the small intestine folded inwardly is not drawn upwardly during operation and the tension applied to the small intestine side is not large, so that it is possible to considerably reduce the potential for constricting the small intestine during the operation. In addition, it is also possible to reduce the bleeding, which may be generated due to the stapling in a state where the tension is applied.

Further, in the circular stapler according to the present invention, since the head section cover is formed to have a small length, preferably, a length of 15 to 18 mm, it is possible to prevent large tension from being applied to the small intestine, and since the inner small intestine is not drawn upwardly, it is possible to keep the inner diameter of the small intestine constant even after the operation. Accordingly, it is possible to considerably reduce the potential for constricting the small intestine during the operation and it is also possible to reduce the bleeding, which may be generated due to the stapling in a state where the tension is applied.

Furthermore, since the detachable cap can be attached to the recessed portion, the circular stapler according to the present invention can be used for end-to-end connection as well as for end-to-side connection during the operation, so that the degree of usage thereof is very high.

While the present invention has been particularly shown and described with reference to exemplary embodiments thereof, the present invention is not limited to the exemplary embodiments. It will be understood by those skilled in the art that various changes in form and details may be made therein without departing from the spirit and scope of the present invention as detailed by the appended claims.

What is claimed is:
1. A circular stapler comprising:
a detachable anvil;
a head section coupled to the detachable the anvil and having a head section cover;
a cylindrical body that longitudinally extends, one end of the cylindrical body is coupled to the head section by a transition section;
an axis extending through a center of the detachable anvil and a center of the cylindrical body; and
wherein a recessed portion in a side surface of the transition section is positioned proximate to the head section cover such that a radial distance from the axis to any point on a surface of the recessed portion is less than a radial distance from the axis to any point on a surface of the cylindrical body and wherein the recessed portion is adapted to receive an inner portion of an intestine.

2. The circular stapler according to claim 1, wherein the head section cover has a circular plate shape.

3. The circular stapler according to claim 2, wherein the head section comprises:
 a cylindrical blade;
 a staple holder having a plurality of staple slots which surround the outer circumferential portion of the cylindrical blade, staples being provided inside the staple slots;
 a push member provided with a protruded portion inserted into the staple slots for pushing the staples; and
 a support positioned under the push member and having a circular plate-shaped top for pushing the push member.

4. The circular stapler according to claim 3, wherein the push member has a circular plate-shaped housing and the protruded portion is formed on the circular plate-shaped housing.

5. The circular stapler according to claim 3, wherein the push member is coupled integrally to the support.

6. The circular stapler according to claim 3, wherein the circular plate-shaped top is made of steel.

7. The circular stapler according to claim 1, wherein the length of the head section cover in a longitudinal direction of the cylindrical body is set to 15 through 18 mm.

8. The circular stapler according to claim 1, wherein the cylindrical body has an arch shape.

9. The circular stapler according to claim 1, further comprising a detachable cap which is coupled and fixed to the recessed portion.

10. The circular stapler according to claim 1, further comprising a shaft which passes through the head section and the cylindrical body and extends long, wherein the diameter of the shaft is set to 1.0 through 1.5 mm.

11. The circular stapler according to claim 1, further comprising a trigger which is provided at a lower portion of the cylindrical body to oppose the recessed portion and which pushes the support.

12. The circular stapler according to claim 1, wherein the recessed portion in the side surface of the cylindrical body is further positioned to receive the circumferential length of at least one tubular tissue.

13. The circular stapler according to claim 1 further comprising means for anastomosing at least two tubular tissue sections connected end to end.

14. The circular stapler according to claim 1 further comprising means for anastomosing at least two tubular tissue sections connected end to side.

15. A surgical stapler comprising:
 a detachable anvil;
 a head section coupled to the detachable the anvil and having a head section cover;
 a cylindrical body that longitudinally extends, one end of the cylindrical body is coupled to the head section by a transition section;
 a cylindrical blade;
 a staple holder having a plurality of staple slots which surround the outer circumferential portion of the cylindrical blade, staples being provided inside the staple slots;
 a push member provided with a protruded portion inserted into the staple slots for pushing the staples;
 a support positioned under the push member and having a circular plate-shaped top for pushing the push member;
 an axis extending through a center of the detachable anvil and a center of the cylindrical body;
 wherein a recessed portion in a side surface of the transition section is positioned proximate to the head section cover such that a radial distance from the axis to any point on a surface of the recessed portion is less than a radial distance from the axis to any point on a surface of the cylindrical body, wherein the recessed portion is adapted to receive an inner portion of an intestine, and wherein the length of the head section cover in a longitudinal direction of the cylindrical body is in a range from 15 mm to 18 mm.

16. The surgical stapler according to claim 15 further comprising a detachable cap which is coupled and releasably fixed to the recessed portion.

17. The circular stapler according to claim 15, wherein the recessed portion in the side surface of the cylindrical body is further positioned to receive the circumferential length of at least one tubular tissue.

18. The circular stapler according to claim 15 further comprising means for anastomosing at least two tubular tissue sections connected end to end.

19. The circular stapler according to claim 15 further comprising means for anastomosing at least two tubular tissue sections connected end to side.

* * * * *